(12) United States Patent  
Goldfain et al.

(10) Patent No.: US 10,092,175 B2  
(45) Date of Patent: Oct. 9, 2018

(54) EYE VIEWING DEVICE ENABLED FOR PERFORMING EAR EXAMINATIONS AND ADAPTER

(71) Applicant: Welch Allyn, Inc., Skaneateles Falls, NY (US)

(72) Inventors: Ervin Goldfain, Syracuse, NY (US); Raymond A. Lia, Auburn, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 774 days.

(21) Appl. No.: 14/620,738

(22) Filed: Feb. 12, 2015

(65) Prior Publication Data

US 2015/0223678 A1 Aug. 13, 2015

Related U.S. Application Data

(60) Provisional application No. 61/938,917, filed on Feb. 12, 2014.

(51) Int. Cl.
| | |
|---|---|
| *A61B 1/227* | (2006.01) |
| *A61B 1/00* | (2006.01) |
| *A61B 3/10* | (2006.01) |
| *A61B 1/06* | (2006.01) |
| *A61B 3/12* | (2006.01) |

(52) U.S. Cl.
CPC .......... *A61B 1/227* (2013.01); *A61B 1/00103* (2013.01); *A61B 1/0669* (2013.01); *A61B 3/10* (2013.01); *A61B 3/1208* (2013.01); *A61B 1/00105* (2013.01); *A61B 1/00163* (2013.01); *A61B 2560/0443* (2013.01)

(58) Field of Classification Search
CPC .................................. A61B 1/227; A61B 3/12
See application file for complete search history.

(56) References Cited

U.S. PATENT DOCUMENTS

| | | |
|---|---|---|
| 3,812,847 A | 5/1974 | Moore et al. |
| D377,393 S | 1/1997 | Sams |
| 5,688,224 A | 11/1997 | Forkey et al. |
| D429,333 S | 8/2000 | Sanders et al. |
| 6,106,457 A | 8/2000 | Perkins et al. |
| 6,165,125 A | 12/2000 | Elliott |

(Continued)

FOREIGN PATENT DOCUMENTS

| | | |
|---|---|---|
| EP | 0 641 540 A1 | 3/1995 |
| GB | 1526228 | 9/1978 |

(Continued)

OTHER PUBLICATIONS

ArcLight; http://www.arclightscope.com/2012/07/otoscope-included/; Date Accessed: Feb. 5, 2013; 2 pages.

(Continued)

*Primary Examiner* — Andrew Yang (57) ABSTRACT

An eye viewing device includes an imaging assembly having at least two optical components disposed along an optical axis of the device. An adapter is attachable to the device and is aligned along the imaging axis of the device, the adapter having at least one adaptive optical element configured for projecting an image of the ear along the imaging axis for viewing without modification to the device and enabling separate examination modes.

11 Claims, 9 Drawing Sheets

(56) References Cited

U.S. PATENT DOCUMENTS

| | | | |
|---|---|---|---|
| 6,202,784 B1 | 3/2001 | Alatriste | |
| 6,830,347 B2 * | 12/2004 | Slawson ................ | A61B 3/125 351/219 |
| 7,029,439 B2 | 4/2006 | Roberts et al. | |
| D566,270 S | 4/2008 | Strom et al. | |
| 7,354,399 B2 | 4/2008 | Strom et al. | |
| 7,784,940 B2 | 8/2010 | Goldfain et al. | |
| 2005/0171399 A1 | 8/2005 | Rich et al. | |
| 2011/0049982 A1 | 3/2011 | Allen et al. | |
| 2012/0245422 A1 | 9/2012 | Hasbun | |

FOREIGN PATENT DOCUMENTS

| | | |
|---|---|---|
| GB | 2491189 | 11/2012 |
| WO | WO 2009/149232 A2 | 12/2009 |
| WO | WO 2012/035351 A1 | 3/2012 |
| WO | WO 2012/158652 A2 | 11/2012 |

OTHER PUBLICATIONS

Welch Allyn 3.5v diagnostic set with ophthalmoscope, Otoscope, rechargeable handle and case—Model 97150M; http://www.amazon.com/Welch-Allyn-Diagnostic-Ophthalmoscope-Rechargeable/dp/B000MOQW10/ref-sr 1 12?e=UTF8&qid=1360001202&sr=8-12 &keywords=ophthalmoscope; Date Accessed: Feb. 4, 2012; 6 pages.

Pro Physician Otoscope ophthalmoscope diagnostic set + protective case!; http://www.amazon.com/Physician-Otoscope-Ophthalmoscope-Diagnostic-Protective/dp/B001FNWOZK/ref=sr 1 1?ie=UTF8&qid=1360001202&sr=8-1&keywords=ophthalmoscope; Date Accessed: Feb. 4, 2013; 6 pages.

http://dig.library.vcu.edu/cdm/ref/collection/mar/id/61; Date Accessed: Feb. 5, 2013; 2 pages.

http://www.amazon.com/Riester-Diagnostic-Otoscope-Ophthalmoscope-2050/dp/B000G5VRSI/ref=cm_cr pr product top; Date Accessed: Feb. 5, 2013; 5 pages.

\* cited by examiner

EYE VIEWING DEVICE ENABLED FOR PERFORMING EAR EXAMINATIONS AND ADAPTER

CROSS REFERENCE TO RELATED APPLICATION

This application claims priority to U.S. Application Ser. No. 61/938,917, entitled: EYE VIEWING DEVICE ENABLED FOR PERFORMING EAR EXAMINATIONS AND ADAPTER, filed Feb. 12, 2014, pursuant to relevant portions of 35 U.S.C. § 119, the entire contents of this document being incorporated by reference.

TECHNICAL FIELD

This application generally relates to the field of medical instruments, and more specifically to an eye viewing (ophthalmic) device that can be adapted to further enable ear (otoscopic) examinations of a patient without significant modification.

BACKGROUND OF THE PRIOR ART

Figure 1A:
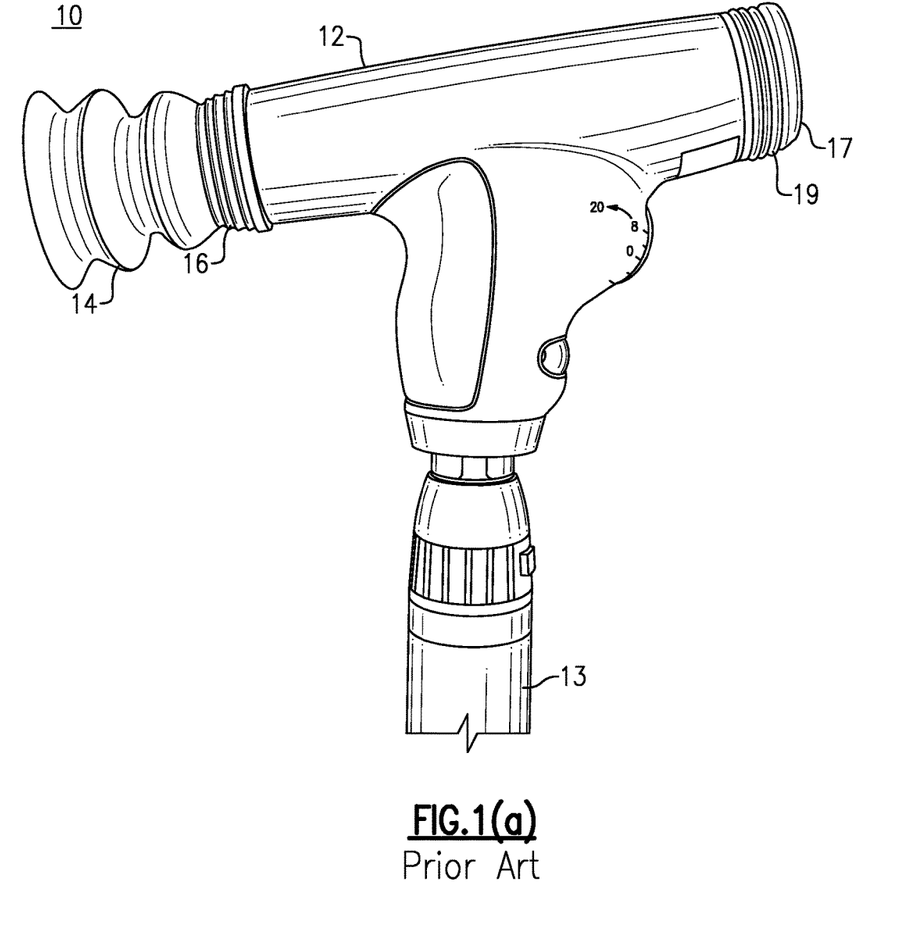
FIG. 1(a) depicts a perspective view of a first known eye viewing device.

Medical instruments that are utilized for conducting routine patient examinations are well known. For example, ophthalmoscopes are diagnostic instruments that are specifically configured for examining various aspects of the eye. A typical direct ophthalmoscope 10, depicted in FIG. 1(a), is defined by an instrument head 12 that is supported by a handle portion 13, the latter having an interior that is configured to retain a set of batteries (not shown) as well as a light source (not shown). A flexible and compressible eyecup 14 is releasably attached to a distal end 16 of the instrument head 12 that directly engages the patient (not shown), with an eyepiece 17 being provided at an opposite proximal end 19 of the instrument head 12. In use, the contained light source (not shown in this view) creates a beam that is directed using contained optics to the distal end 16 of the device 10 and onto the eye of a patient (not shown). Reflected light, in the form of an image of the back of the eye, is then transmitted along a contained imaging assembly of the instrument 10 to the eyepiece 17 for viewing by a caregiver (not shown).

Figure 1B:
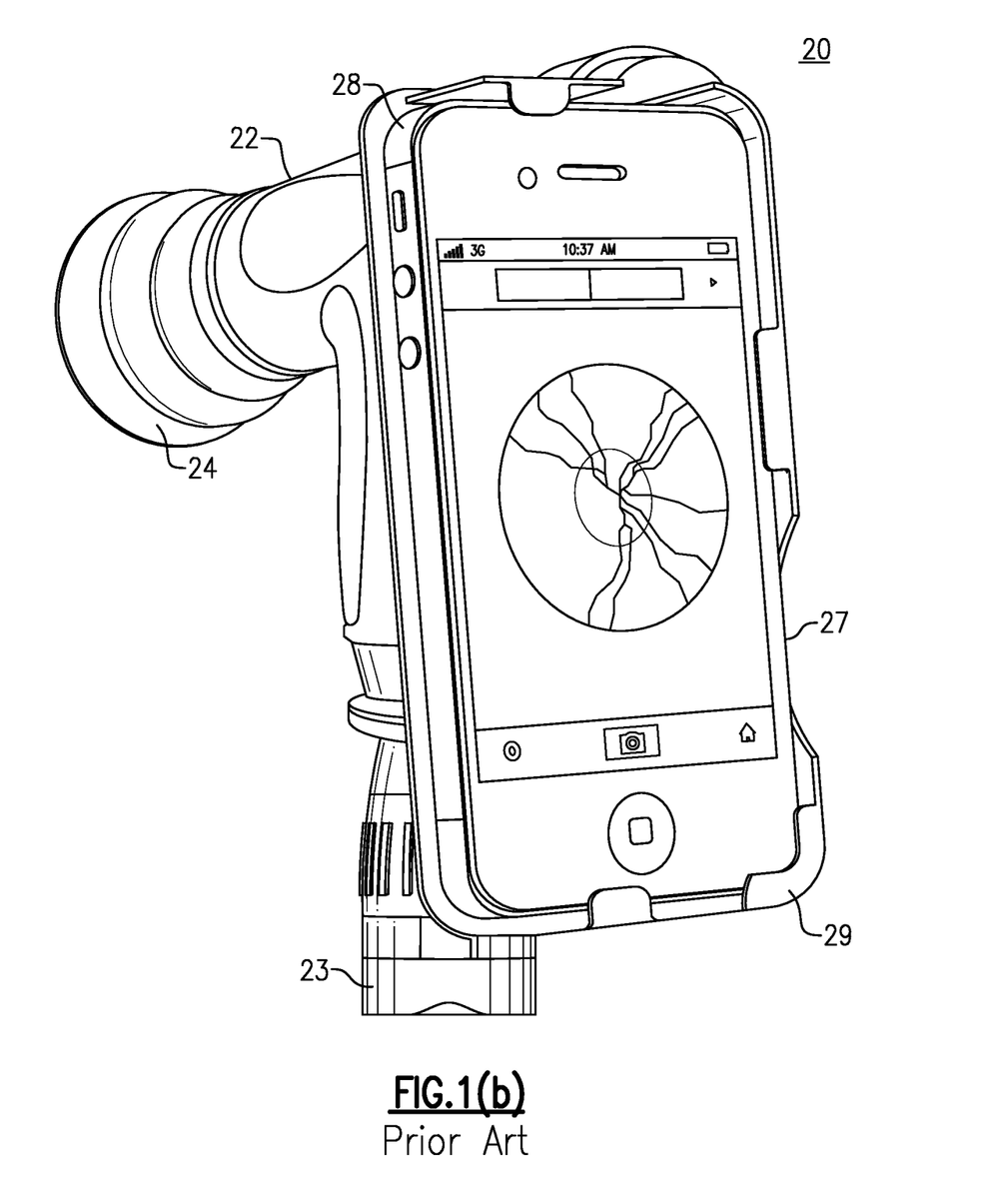
FIG. 1(b) depicts a perspective view of a second known eye viewing device.

Alternatively, a similarly configured ophthalmoscope 20 having an instrument head 22 and a handle portion 23 can utilize an electronic imaging device 27, such as a smartphone, as shown in FIG. 1(b), which can be attached to a holding or support fixture 28 that engages the proximal end 29 of the instrument head 22 in lieu of an eyepiece, the instrument head 22 further supporting an eyecup 24 to interface with the patient. Accordingly and in operation, an image of the eye can be captured and transmitted via a contained imaging system to the contained imager of the attached device 27. Specific details relating to the foregoing eye viewing instruments are described in U.S. Pat. No. 7,784,940 B2, incorporated by reference herein in its entirety.

Figure 2A:
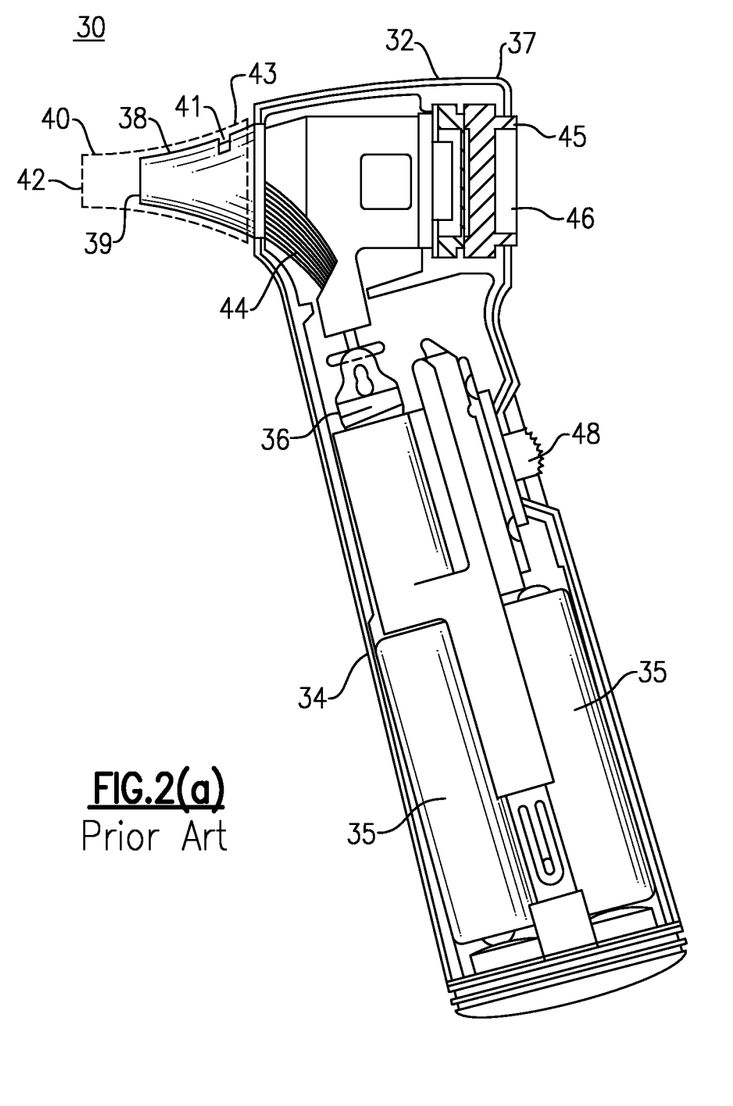
FIG. 2(a) is a perspective view of a first known ear viewing device.

Examinations of the ear are also a common procedure that is conducted during routine patient visits by a caregiver using an otoscope. A typical otoscope 30, illustrated in FIG. 2(a), includes an instrument head 32 that is attached to a handle portion 34 having an interior sized to accommodate a set of batteries 35, as well as a light source, such as an incandescent lamp 36. An axisymmetric insertion portion 38 extending from the distal end 39 of the instrument head 32 is configured to receive a disposable speculum tip or tip member 40 (shown in phantom), the latter being a hollow disposable component defined by an axisymmetric configuration having a distal tip opening 42 and an opposing proximal tip opening 43. The speculum tip 40 includes an internal feature (not shown) that is sized to engage a circumferential bayonet slot 41 formed on the exterior of the axisymmetric insertion portion 38. The speculum tip 40 is further defined by a conical tapering configuration that prevents the speculum tip 40 from being inserted beyond a predetermined distance into the ear canal (not shown) of a patient. The proximal end 37 of the instrument head 32 is provided with a viewing window 45 that can include a magnifying optic 46. In use, the contained incandescent lamp 36 is illuminated using a switch 48 located on the handle portion 34 and emitted light is directed to the speculum tip 40 using a set of optical fibers 44 having a polished proximal end that is coupled in relation to the incandescent lamp 36. The distal end (not shown) of the optical fibers 44 are disposed to encircle the distal opening 39 of the axisymmetric insertion portion 38. This transmitted light is then circumferentially directed through the distal tip opening 42 of the attached speculum tip 40, the latter having a polished interior surface to promote transmission, to enable viewing of the patient's ear canal and the tympanic membrane (not shown). This light is reflected for viewing by a caregiver at the viewing window 45 to determine the presence of infections, including otitis media.

Figure 2B:
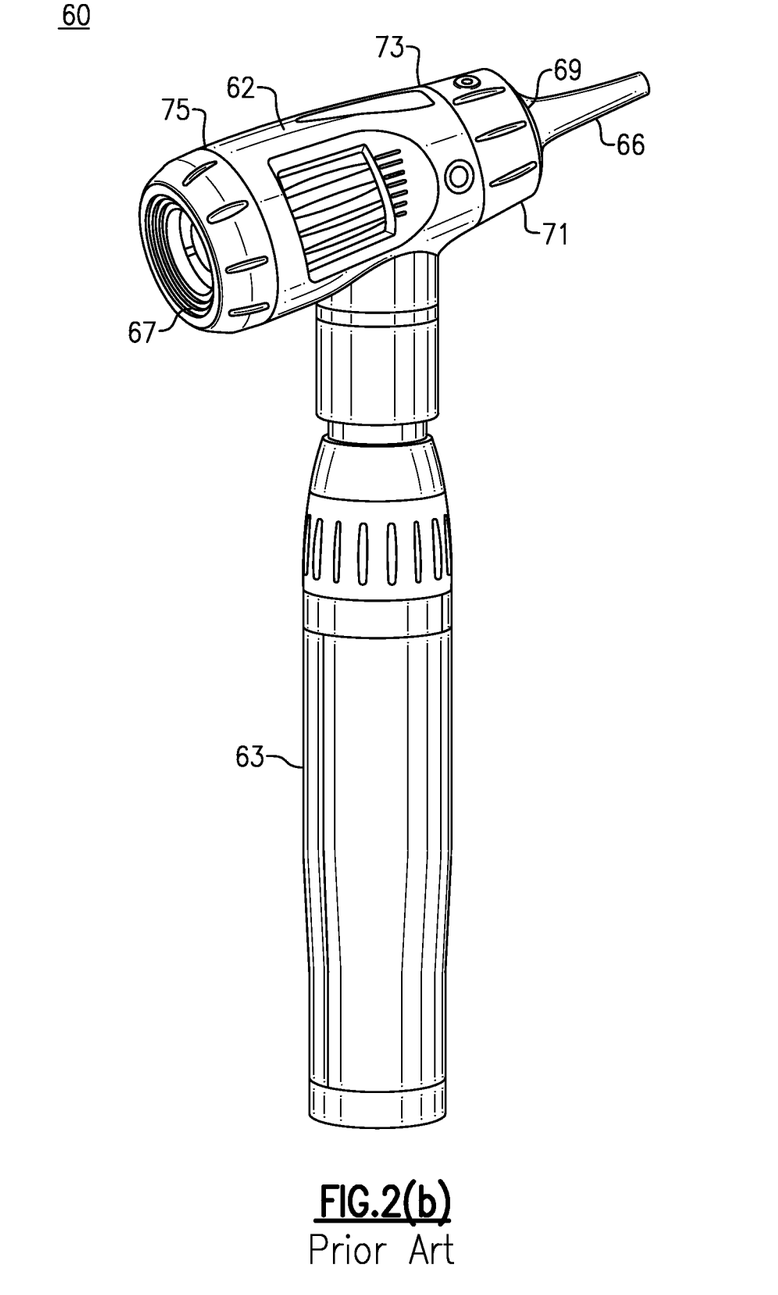
FIG. 2(b) is a perspective view of a second known ear viewing device.

More recently, otoscopes 60 have been developed including optical assemblies disposed within the instrument head that enable enhanced viewing by a caregiver or through an attached electronic imaging device. One example, depicted in FIG. 2(b), is manufactured and sold under the tradename of Macroview by Welch Allyn, Inc. and further described in U.S. Pat. No. 7,399,275, incorporated herein in its entirety by reference. This instrument 60 includes an instrument head 62 that is attached to the upper end of a handle portion 63, the latter retaining a set of rechargeable batteries (not shown), as well as a light source (not shown), such as an LED or lamp. As in the preceding, a speculum tip or tip member 66 is releasably attached to a distal end 73 of the instrument head 62, the speculum tip 66 being defined by a tapering axisymmetric configuration that is hollow and further defined by opposing distal and proximal tip openings. In this instrument version, the proximal end of the speculum tip 66 includes a set of exterior circumferential mounting features 69 that are configured to releasably engage a corresponding set of arcuate slots (not shown) provided in an attachment member 71, the latter being integral to the distal end 73 of the instrument head 62 and disposed in lieu of an axisymmetric insertion portion. The speculum tip 66 is attached by aligning the slots in the attachment member 71 with the proximal mounting features 69, the attachment member 71 being rotatable to effect release of the speculum tip 66.

According to this example, an optical assembly disposed within the interior of the instrument head 62 is configured to create a larger field of view that permits the entire tympanic membrane to be viewed at once, either directly by a caregiver at an eyepiece 67 or alternatively to an electronic imaging device (not shown) attached to the proximal end 75 of the instrument head 62 and aligned with the contained optical assembly. Details regarding the tip attachment mechanism and the operational features of this instrument 60 are provided in the above noted and incorporated '275 patent.

There has been a general pervasive need in the medical field to provide versatility and functionality in diagnostic instruments. For example, both eye viewing and ear viewing devices are commonly used in a single patient examination. Various attempts at instrument consolidation have previously been attempted. For example, Applicants previously invented a single diagnostic instrument as described in U.S. Pat. No. 6,106,457, the entire contents of which are herein incorporated by reference. According to the teachings of this latter '457 patent, a digital camera can be configured with multiple instrument heads that are separately and interchangeably attachable for permitting otological, ophthalmic, skin microscopy and other examinations to be conducted. Each of the separate instrument heads, as described by the '457 patent, however, require a unique optical system and in certain instances may further require a unique illumination system for conducting various examinations of a patient.

As noted, there is a general and continuing need in the field to provide additional versatility and functionality within a single medical diagnostic instrument.

BRIEF DESCRIPTION

Therefore and according to one aspect, there is provided an examination instrument for examining the eye, the examination instrument comprising a housing having a proximal end and a distal end. An illumination assembly disposed within the instrument housing includes a light source and is configured to direct a light beam along an illumination axis towards the distal end of the instrument housing. An imaging assembly, also disposed in the instrument housing, comprises at least two optical components disposed along an imaging axis of the instrument that enables examination of the eye. An adapter is releasably attachable to the housing. The adapter can include at least one optical element that is aligned with the imaging axis of the instrument and optically coupled to the imaging assembly, when attached, to enable imaging of the ear of a patient such that the instrument is configured to operate in either a first eye examination mode or a second ear examination mode.

According to at least one version, the adapter comprises a speculum tip member having a distal end and an opposing proximal end, the tip member being defined by an axisymmetric configuration including a hollow interior that retains the at least one optical element. When the adapter is attached to the instrument housing, the at least one contained optical element is aligned with the imaging axis of the instrument. The at least one optical element cooperates with the imaging and illumination assemblies of the instrument and enables otoscopic examinations when the adapter is attached to the instrument and a patient interface portion (i.e., the speculum tip member) of the adapter is positioned within the ear of a patient.

In one version, the adapter comprises an attachment member that is releasably attachable to the distal end of the eye viewing device. In another version, the adapter can be integrated within the instrument. The attachment member can further be configured for supporting the at least one optical element and for enabling attachment of the speculum tip member. Alternatively, the speculum tip member can be directly integrated with the adapter. In one version, the attachment member is defined by a conically shaped distal portion having at least one feature for releasably engaging the speculum tip member and in which the at least one optical element is supported in a predetermined orientation at a distal opening of the attachment member. In one version, the optical element is supported in an orientation that is angled relative to the imaging axis of the instrument to reduce the effect of glare. The optical element can be integrated with the adapter such as through a molding process, or can be fixedly secured within the adapter using a press fit or adhesives. In one described embodiment, the attachment member can be re-used with the eye viewing device for each ear examination while the speculum tip member can be configured for single patient or single use and can be discarded following an examination. Alternatively, the entire adaptive module can be manufactured as a disposable.

In accordance with another aspect, there is provided an otoscopic module configured for attachment to an eye viewing device, the otoscopic module comprising a hollow axisymmetrical tip member having a distal end and an opposing proximal end and at least one adaptive optical element disposed within the interior of the tip member. When attached to an eye viewing device, the otoscopic module is configured for alignment with an optical axis of the eye viewing device, in which the tip member receives illumination from the eye viewing device to permit imaging of the ear. In one version, the otoscopic module comprises an attachment member that is releasably attachable to the eye viewing device and supports the at least one adaptive optical element in a preferred orientation. The attachment member can permit releasable attachment of the hollow tip member and includes at least one feature to reliably attach and align the at least one optical element with the imaging and illumination assemblies upon attachment to the instrument. In another version, the hollow tip member can be directly integrated with the remainder of the module.

In accordance with yet another aspect, there is disclosed a method for enabling an eye viewing device to conduct otoscopic examinations therewith, the method comprising:

providing an eye viewing device having an imaging assembly and a defined imaging axis; and providing an adapter that is fittable to a distal end of the eye viewing device, the adapter including at least one optical element disposed therein that is configured for alignment with an imaging axis of the eye viewing device when the adapter is attached thereto.

According to at least one version, the adapter can include an attachment member that enables attachment to the eye viewing device and also supports at least one adaptive optic. A patient interface in the form of a speculum tip member can be attached to the attachment member. According to one version, the speculum tip member is releasably attached to the adapter. According to another version, the speculum tip member can be integrated with the remainder of the adapter. At least one adaptive optic is arranged to receive illumination from a contained illumination assembly of the eye viewing device. According to at least one version, the adaptive optic is angled relative to the imaging axis to reduce the incidence of glare.

A number of advantages can be realized using an instrument which is configured as presently described. First, significant versatility is achieved by enabling reliable patient examination of the eyes and ears of a patient using a single instrument having a dedicated imaging and illumination assemblies. Both ophthalmic and otoscopic examinations can be performed sequentially using the same instrument through selection of patient interfaces (i.e. an eye cup or speculum tip element).

Yet another advantage that is realized is that of savings in terms of cost, as well as available shelf space, through use of a single medical diagnostic instrument having multiple functionalities that can be performed reliably.

These and other features and advantages will be readily apparent to those of sufficient skill when reading the following Detailed Description, which should be read in conjunction with the accompanying drawings.

DETAILED DESCRIPTION

The following describes an exemplary embodiment of a medical examination instrument (i.e., eye viewing device), which is preferably portable to permit preferably hand-held operation and further configured to enable comprehensive examinations of both the eye and ear without significant modification to the instrument. According to this specific embodiment, a releasably attachable adaptive module or adapter utilizes the optical system of an eye viewing device in order to enable ear examinations without further modification. It will be readily apparent that other versions or variations can be created that utilize the inventive concepts that are discussed herein. In addition and throughout the course of this discussion, several terms are frequently used in order to provide a suitable frame of reference in regard to the accompanying drawings. These terms, which include "distal", "proximal", "above", "below", "horizontal", "vertical", "upper", "lower" and the like, however, are not intended to be limiting with regard to the invention, except where explicitly indicated.

Figure 3:
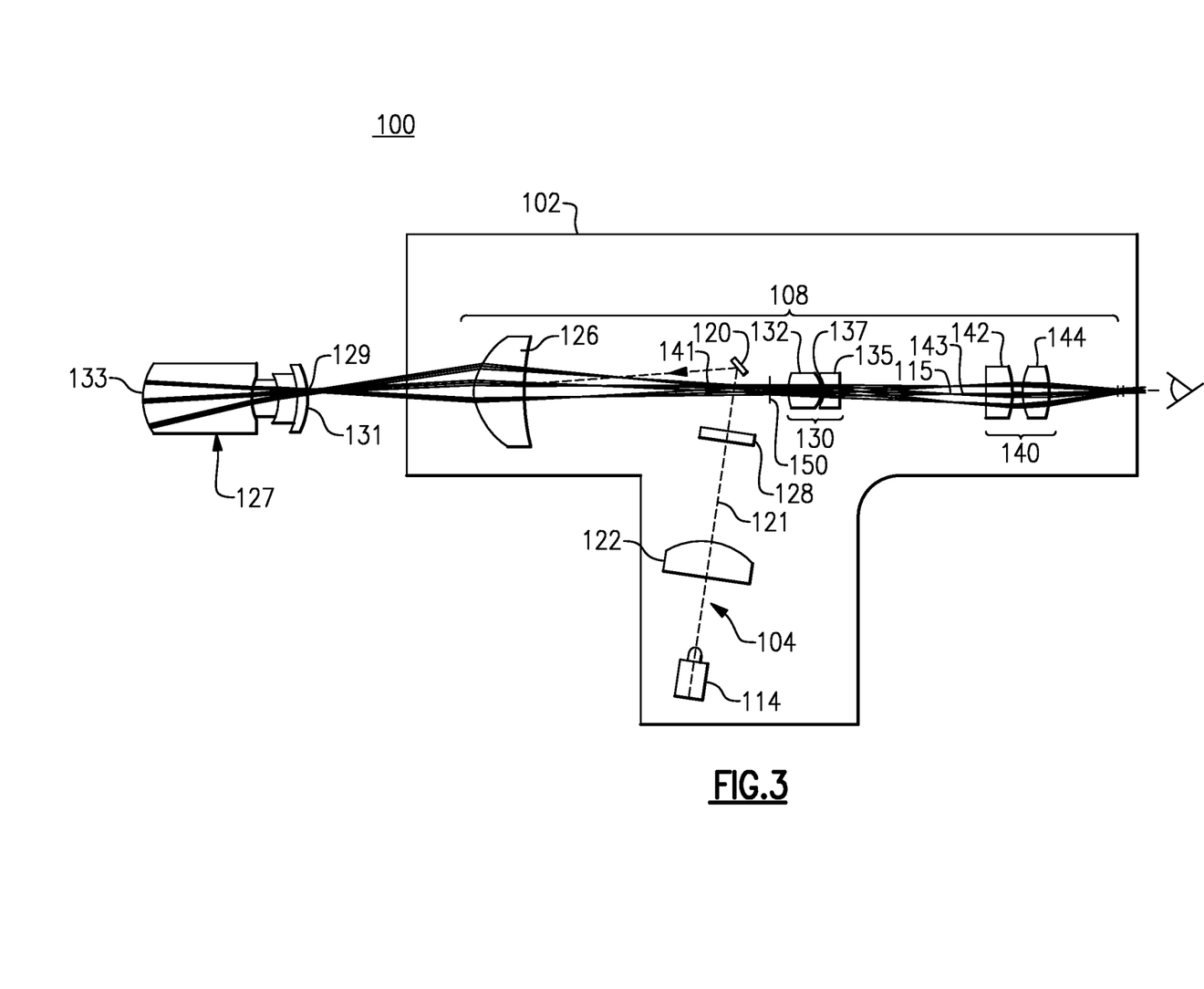
FIG. 3 is diagrammatic view of an eye viewing device in accordance with an exemplary embodiment and configured in an eye examining mode.

An exemplary eye viewing device 100 that is configured for use with an adaptive module or adapter in accordance with this application is depicted in FIG. 3, and is similar to the instruments depicted in FIGS. 1(a) and 1(b). The device 100, as described herein, is capable of operation in a first eye viewing/examination mode and an additional second ear viewing/examination mode following attachment of the adapter. The first eye examination mode configuration is first discussed with reference to FIG. 3 with regard to contained illumination and imaging assemblies, 104, 108, respectively, each assembly being disposed within an instrument head 102. The instrument head 102 is defined by a hollow interior sized for accommodating the assemblies 104, 108.

The illumination assembly 104 for the herein described device 100 includes a light source 114, a condenser lens 122 and an objective lens 126, the latter optic being positioned forward (distal) of the light source 114 along a defined illumination axis 121 for converging light rays that are emitted by the light source 114.

The light source 114 according to this specific embodiment includes at least one filament-based lamp. Alternatively, the light source 114 can be an arc lamp, a fiber optic light source or a solid state light source such as at least one LED, such as a white or multispectral LED. The light source 114 is preferably aligned about 90 degrees relative to a defined viewing or imaging axis 115 of the device 100. It should be further noted that the source of illumination and illumination assembly is not limited to this configuration. Examples of other disposed illumination assemblies are described in U.S. Patent Application Publication No. 2010/0231856A1, incorporated herein in its entirety by reference.

In accordance with this embodiment, a reflective element such as a mirror 120 is disposed along the illumination axis 121 in association with the light source 114 and the condenser lens 122, the latter optical component being configured to converge the emitted light from the light source 114 onto the mirror 120. Each of the foregoing elements further operate in conjunction with the objective lens 126 to project an image of the light source 114 onto or near a patient's cornea, schematically shown as 131, when the device 100 is used in the eye viewing examination mode. According to this version, a linear polarizer 128 is further disposed along the defined illumination axis 121 to reduce the effects of glare.

According to this known version, details of which are further described in previously incorporated U.S. Patent Application Publication No. 2010/0231856A1, the light emitted by the light source 114 is directed along the illumination axis 121, in which the light rays are further narrowed by the condenser lens 122 and reflected by the mirror 120, which is mounted at a suitable angle from the imaging axis 115 relative to the objective lens 126. The orientation of the light source 114 matches the geometry of the mirror 120, thus minimizing the size of the mirror 120.

The objective lens 126 works in combination with the condenser lens 122 to project an image of the light source (e.g., a lamp filament) 114 onto the patient's cornea 131. The objective lens 126 and the cornea 131 also form a part of the imaging assembly 108 of the herein described device 100 relative to a patient's eye, shown schematically herein as 127.

More specifically and still referring to FIG. 3, the imaging assembly 108 includes the objective lens 126, an imaging lens(es) 130 and an eyepiece lens(es) 140. A retinal image focal plane 141 is produced intermediate the objective lens 126 and the imaging lens 130, while an eyepiece focal plane 143 is produced intermediate the imaging lens 130 and the eyepiece lens 140. The imaging assembly 108, according to the depicted version, further includes the imaging axis 115 on which each of the lenses 126, 130 and 140 are substantially centered.

The light rays crossing the retinal focal plane 143 consists of light rays that enter the eye 127 through the pupil 129, each shown schematically in FIG. 3 and which are reflected from the retina 133 at the back (fundus) of the eye through the pupil 129. Since small undilated pupils tend to inhibit the transmission of both incident into an eye and reflected retinal image light out of the eye, retinal images viewed through undilated pupils are readily obscured by glare (which is especially prevalent when retinas are viewed through undilated pupils, since incident light is more likely to be reflected from highly reflective outer eye structures). In addition to glare attribution to light being reflected from the outer eye structures, such as the iris and sclera, retinal images can be obscured by glare attributable to other sources such as light that is reflected from a patient's cornea (corneal glare) and light that is reflected from a component of the eye viewing device such as a lens of the device (internal glare).

To that end, the eye viewing device 100 according to this version is adapted for viewing images through an undilated pupil and in which the device preferably includes features that operate to reduce such glare, and in doing so reduce the percentage of received light rays not corresponding to a retinal image relative to the percentage of received light rays corresponding to a retinal image.

Still referring to FIG. 3, an aperture stop 150 is positioned forward of the imaging lens 130 to block unwanted light. The aperture stop 150 is preferably positioned substantially coaxially with the imaging axis 115 and substantially conjugate to a patient's pupil when in an operative position in relation to the device 100. The positioning of the aperture stop 150 in a position that is substantially coaxial with the imaging axis 115 encourages substantially a maximum amount of useful receive imaging light to be admitted through the imaging lens 130 without also admitting glare light that originates radially outside the patient's pupil. By positioning the aperture stop 150 so that it is substantially conjugate to a pupil 129, the aperture stop 150 acts to block light that is reflected from various outer eye structures, such as the iris and sclera. Because the apex of the cone of light generated by the illumination assembly 106 is substantially conjugate to a patient's pupil for positioning the device 100 in an operative position, and because the preferred position of the aperture stop 150 is also one that is conjugate to the pupil 129, the aperture stop 150 can therefore be described as one that is substantially conjugate to the apex of the cone of light generated by the illumination assembly 104.

In the herein described imaging assembly 108, retinal light rays pass through the pupil 129 in a collimated formation. The objective lens 126 focuses the parallel light from the patient's eye 127 to the retinal image focal plane 141 disposed between the objective lens 126 and the aperture stop 150. According to this specific design, the aperture stop 150 operates to block light that originates outside of a 2 mm diameter circle located about 25 mm from the objective lens 126. This is the location of a patient's pupil 129 when the device 100 is in a nominal operating position.

A linear polarizer (not shown) disposed along the imaging axis 115 operates in concert with the linear polarizer 128 of the illumination assembly 106 in order to reduce the incidence of internal and external glare and especially internal glare from the objective lens 126 and external glare attributable to corneal reflections. The linear polarizer of the imaging assembly 108 and the linear polarizer 126 of the illumination assembly 106 of the herein described device 100 are preferably disposed in a cross-polarized configuration.

The imaging lens 130 according to this specific embodiment is defined by two lens elements and more specifically, a first lens element 132 and a second lens element 135 forming a doublet. These lens elements 132, 135 are separated by an intermediate air gap 137. The imaging lens 130 images the retinal image focal plane 141 of the objective lens 126 to the eyepiece focal plane 143.

A field stop (not shown) sized to correspond to the field of view may be disposed at the eyepiece focal plane 143. The retinal image focal plane 141 and the eyepiece focal plane 143 are conjugate to the retinas of the patient and viewer, respectively.

The eyepiece lens 140 comprises two lens elements; namely, lenses 142 and 144 each aligned along the imaging axis 115 of the device 100 that are configured to direct light to the proximal end of the instrument head 102 for viewing, either through an eyepiece or an attached imager (not shown). Additional details regarding the design and operation of this instrument are provided in U.S. Pat. No. 6,527,390, the entire contents of which are herein incorporated by reference.

Figure 4:
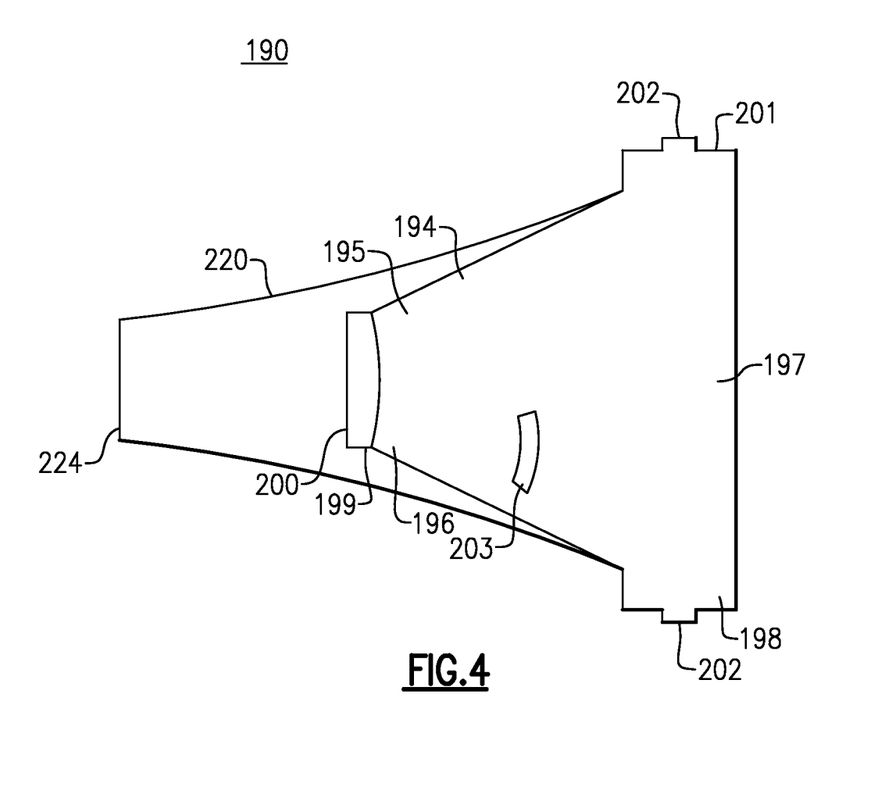
FIG. 4 is a side elevational view of an adapter for use with the eye viewing device of FIG. 3 and in accordance with an exemplary embodiment.

Referring to FIG. 4, an adaptive module or adapter 190 is shown for attachment to the herein described device 100. According to this specific embodiment, the adaptive module 190 is releasably attachable to the front or distal end of the herein described device 100 and comprises an attachment member 194 and a speculum tip member 220. The attachment member 194 is defined by an axisymmetric portion 195 at its distal or front end 196 and an attachment portion 197 provided at an opposing proximal or rear end 198. The axisymmetric portion 195, according to this specific embodiment, is defined by a tapering conical configuration that outwardly expands from the distal end 196 toward the proximal end 198. The attachment portion 197 includes an annular proximal portion 201 having at least one circumferential engagement member, such as an engagement tab 202, that is configured to engage a corresponding slot (not shown) formed at the distal end of the instrument 100. A single or series of engagement tabs 202, disposed in a circumferential configuration, can be provided for engagement with a corresponding number of slots.

According to this exemplary embodiment, at least one adaptive optical element 200 is fixedly secured using a press fit or suitable adhesives to the distal end 196 of the attachment member 194 and more specifically to a distal tip opening 199 of the conical axisymmetric portion 195. Alternatively, the adaptive optical element 200 can be manufactured with the remainder of module as an integrated component, formed, for example by a molding process. According to this embodiment a single adaptive optical element 200 is provided, which is made from BK7 glass. However, this adaptive element 200 can alternatively be made from a clear plastic or other optically transmissive materials. More specifically, the adaptive optical element 200 includes a plano distal surface 204 and a curved proximal surface 206. According to this specific embodiment, the adaptive optical element 200 has a center thickness of about 1.6 mm and an outer diameter of about 6 mm and wherein the curved proximal surface 206 is defined by a radius of curvature of about −18.61 mm.

The attachment member 194 is configured to releasably engage the speculum tip member 220 which can be attached in overlaying relation. Alternatively, the attachment portion 197 and the speculum tip member 220 could be integrally formed as a single component. For purposes of this embodiment, the speculum tip member 220 is similar in terms to the version depicted at FIG. 2(a) and is hollow, including a distal tip opening 224. The exterior of the conically shaped axisymmetric portion 195 includes a circumferential slot 203 that is configured to engage an internal rib feature (not shown) provided within the interior of the speculum tip member 220 in which the speculum tip 220 is retained by twisting the speculum tip member 220 in one direction in a formed bayonet-like connection.

Referring to FIG. 4, the adaptive optic element 200 is mounted at an onto a support formed at the distal end of the conical axisymmetrical portion 195 of the attachment member 194. In a preferred version, the adaptive optical element is tilted by a small angle (about 5 degrees relative to the imaging axis 115) in order to reduce surface reflections of the illumination from the lens from appearing in the resulting image. It will be readily apparent that other mounting configurations can be utilized. As discussed previously, the adaptive optical element 200 can be attached to the support using a press or interference fit or suitable adhesives. Alternatively, the entire module 190, including the adaptive optical element 200, can be made from the same material and integrally formed, such as using a molding process. The module 190 can therefore be discarded following a single use or single patient use, according to one version. It may also be possible, according to another version, for the adapter 190 to be removed and reused, depending on the choice of material(s).

Figure 5:
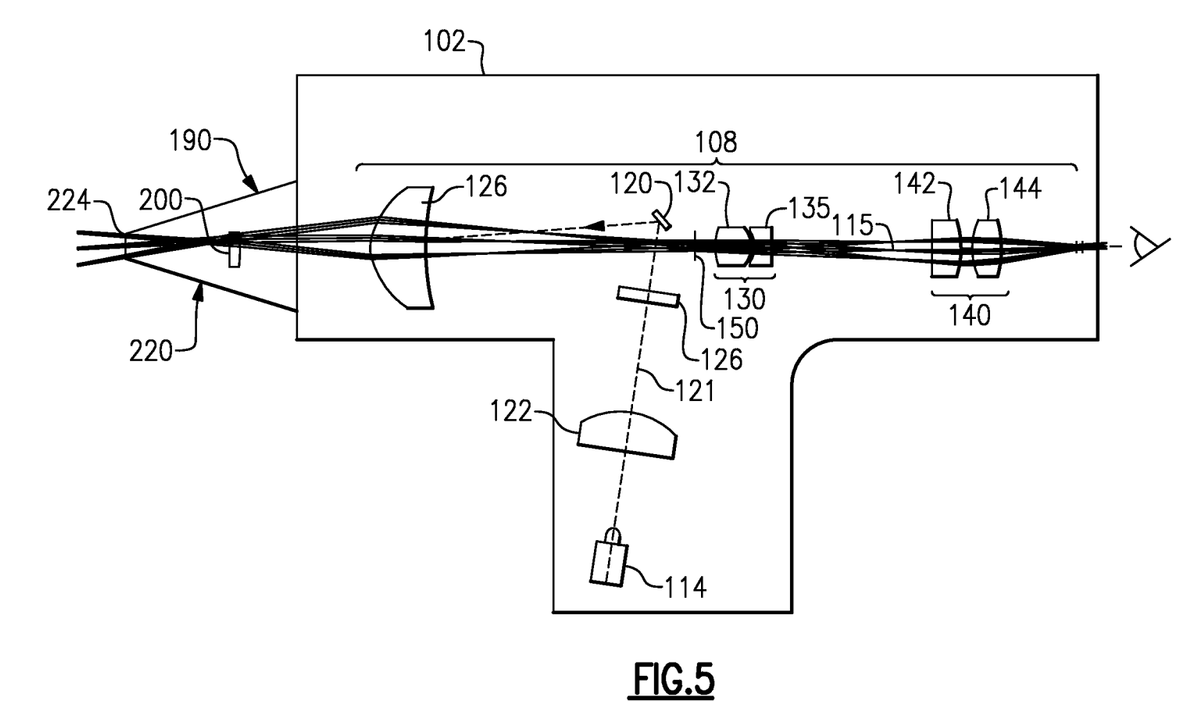
FIG. 5 is a schematic layout of the eye viewing device of FIG. 3 as configured with the adapter of FIG. 4 for enabling the device to be further configured in an ear examining mode.
Figure 6:
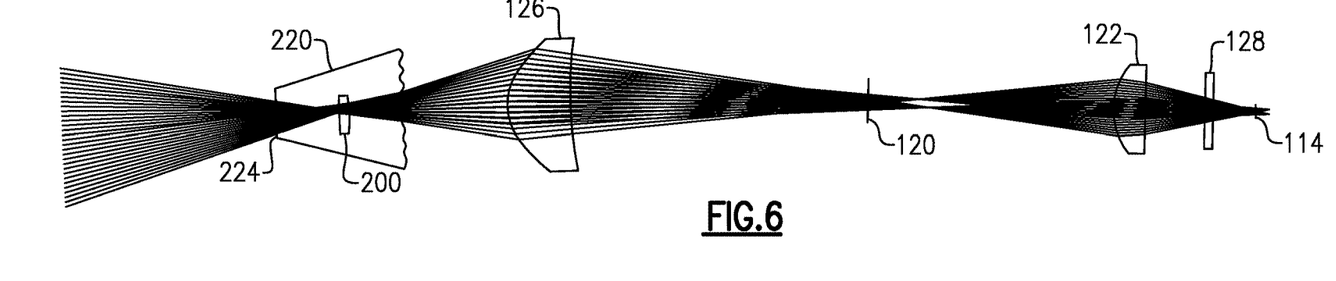
FIG. 6 illustrates a schematic view of the illumination assembly of the device of FIG. 5.
Figure 7:
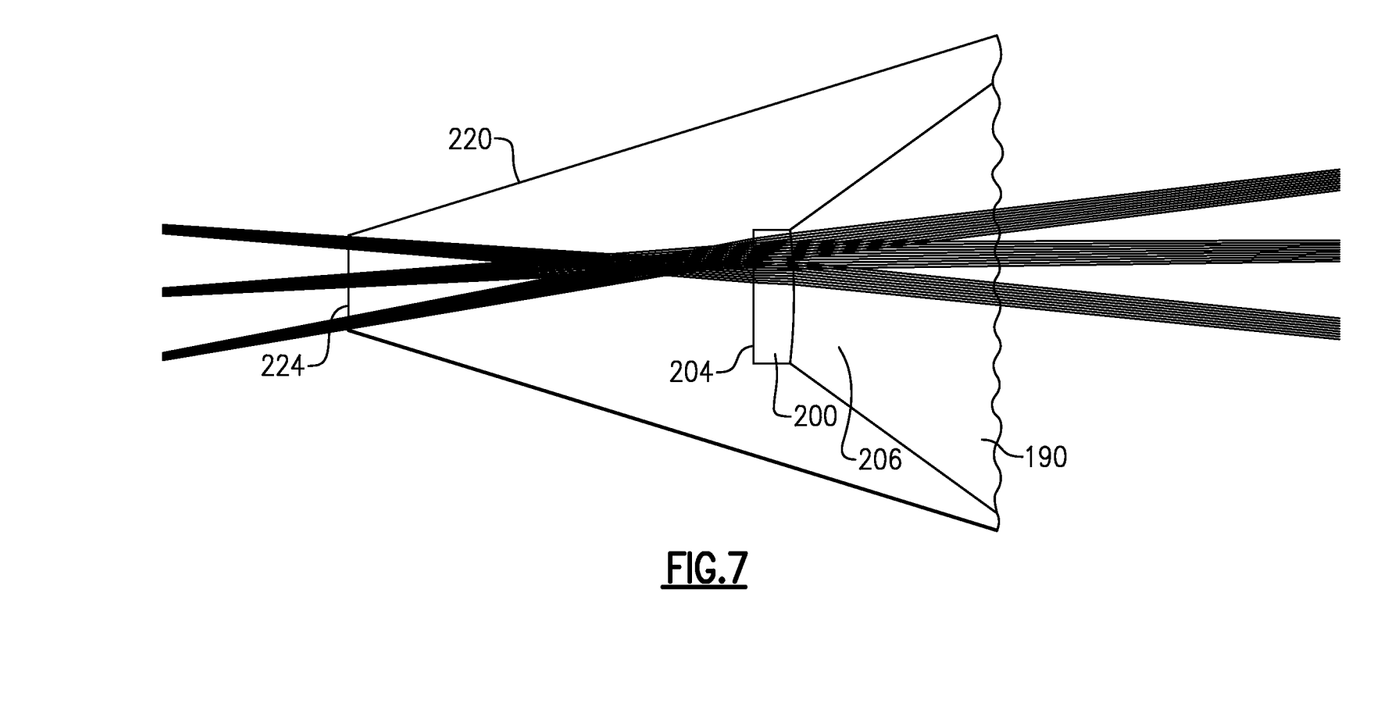
FIG. 7 is an enlarged view of a portion of the illumination assembly of FIG. 6.

To operate in an ear examination mode and when the module is assembled as shown in FIGS. 5-7, the distance between the distal tip opening 228 of the speculum tip member 220 and the distal plano surface 204 of the adaptive optical element 200 is about 17.6 mm, the distance between the objective lens 126 and the curved proximal surface 206 of the adaptive optical element 200 is about 24.5 mm and the distance between the distal tip opening 224 of the speculum tip member 220 and the tympanic membrane (not shown) of a patient is about 18 mm.

The herein described adapter 190 is configured to be releasably attached to the device 100 in lieu of a compressible eye cup 14, FIG. 1, which can be releasably removed from the distal end of the instrument head 102. In terms of structure and manufacture, it should be noted that a number of variations can be easily contemplated while providing duality of examination modes.

In terms of operation when assembled, the adapter 190 cooperates with the contained illumination and imaging assemblies 104, 108, as shown schematically in FIGS. 5 and 6. More specifically, the light source 114 emits a light beam that is directed through the condenser lens 122 and linear polarizer 128 to the angled mirror 120 along the illumination axis 121, which directs the light through the objective lens 126 and through the slightly tilted adaptive optical element 200 of the attached adapter 190. An unfolded view of the illumination assembly is depicted at FIG. 6 and an enlarged schematic view of the light as it passes through the adaptive optical element 200 is shown in FIG. 7. In the foregoing figures and for reasons of clarity, only the speculum tip member 220 and adaptive optical element 200 of the adapter 190 are depicted.

Reflected light from the interior of the ear (not shown) is transmitted along the imaging axis 115 of the instrument 100 in which the light passes through distal tip opening 224 of the attached speculum tip member 220, through the adaptive optic element 200 of the module 190 and is caused to converge through the objective lens 126 of the device 100. The reflected light continues to pass through the objective lens 126 and is further directed through the aperture stop 150. The angled mirror 120 is sufficiently out of the optical path and is not aligned with the imaging axis 115 to interfere with the reflected image. The light continues to travel through the imaging lenses 130 and the eyepiece lenses 140 to the proximal end of the device 100, which includes either the eyepiece or an electronic imaging device (not shown).

PARTS LIST FOR FIGS. 1-7

10 ophthalmoscope
12 instrument head
13 handle portion
14 eyecup
16 distal end
17 eyepiece
19 proximal end
20 ophthalmoscope
22 instrument head
23 handle portion
24 eyecup
26 distal end
27 imaging device
28 holding or supporting fixture
29 proximal end
30 otoscope
32 instrument head
34 handle portion
35 batteries, set
36 incandescent lamp
37 proximal end
38 axisymmetric insertion portion
39 distal end
40 speculum tip
41 circumferential slot
42 distal end
43 proximal end
44 optical fibers
45 viewing window
46 magnifying optic
48 switch
60 otoscope
62 instrument head
63 handle portion
66 speculum tip member
67 eyepiece
69 mounting features
71 attachment member
73 distal end
75 proximal end
100 eye viewing device
102 instrument head or housing
104 illumination assembly
108 imaging assembly
114 light source
115 imaging axis
120 mirror
121 illumination axis
122 condenser lens
126 objective lens
127 eye
128 linear polarizer
129 pupil
130 imaging lens
131 cornea
132 lens
133 retina
135 lens
137 air gap
140 eyepiece lens
141 retinal focal plane
142 lens
143 eyepiece focal plane
144 lens
150 aperture stop
154 first lens element
158 second lens element
162 intermediate air gap
190 adaptive module or adapter
194 attachment member
195 conical axisymmetric portion 196 distal end
197 attachment portion
198 proximal end
199 distal tip opening
200 adaptive optical element
201 annular proximal end
202 engagement tab
203 circumferential slot
204 plano distal surface
205 engagement tab
206 proximal curved surface
220 speculum tip member
224 distal tip opening It will be readily apparent that other versions and modifications to the herein described concepts could be derived by one of ordinary skill in the field that embody the inventive concepts discussed herein and in accordance with the following claims.

The invention claimed is:

1. An eye viewing device comprising:
   a housing having a proximal end and a distal end;
   an imaging assembly comprising at least two optical components disposed along an imaging axis of the device; and
   an adapter releasably attachable to the distal end of the housing, wherein the device is thereby configured to selectively and independently operate in a first eye examination mode and a second ear examination mode, the adapter including at least one optical element aligned with the imaging axis when the adapter is attached to the housing.

2. An eye viewing device according to claim 1, further comprising an illumination assembly including a light source aligned along an illumination axis and in which the at least one optical element of the adapter is aligned along each of the imaging and illumination axes of the device when the adapter is attached to the housing.

3. The eye viewing device according to claim 2, wherein the illumination assembly includes an angled mirror aligned along the illumination axis and configured to direct light from the light source angled in relation to the imaging axis of the device.

4. The eye viewing device according to claim 2, wherein the adapter comprises a speculum tip member.

5. The eye viewing device according to claim 4, wherein the speculum tip member is releasably attachable to the adapter.

6. The eye viewing device according to claim 4, wherein the speculum tip member is integral with the adapter.

7. The eye viewing device according to claim 4, wherein the at least one optical element is fixedly attached to the adapter.

8. The eye viewing device according to claim 4, wherein the at least one optical element is integrated with the adapter and formed as a single component.

9. The eye viewing device according to claim 4, wherein the adapter includes an attachment member that is releasably attachable to the device and further includes at least one feature for enabling releasable attachment of the speculum tip member.

10. The eye viewing device according to claim 6, wherein the adapter is configured or single or single patient use.

11. The eye viewing device according to claim 4, wherein the at least one optical element of the adapter is tilted relative to the imaging axis to reduce the effect of surface reflections off the at least one optical element.

* * * * *